of Germany

United States Patent [19]
Uhrhan et al.

[11] 4,080,399
[45] Mar. 21, 1978

[54] SULPHENAMIDES, THEIR PRODUCTION AND THEIR USE AS VULCANIZATION RETARDERS

[75] Inventors: Paul Uhrhan, Cologne; Ernst Roos, Odenthal-Osenau; Manfred Abele, Porz-Wahn; Rudiger Schubart; Theo Kempermann, both of Cologne, all of Germany

[73] Assignee: Bayer Aktiengesellschaft, Germany

[21] Appl. No.: 650,305

[22] Filed: Jan. 19, 1976

[30] Foreign Application Priority Data

Jan. 23, 1975 Germany .............................. 2502656

[51] Int. Cl.$^2$ .................... C07D 209/34; C08F 28/00
[52] U.S. Cl. ............................... 260/784; 260/79.5 P; 260/326 S; 260/326 H
[58] Field of Search ............... 260/784, 326 S, 326 H, 260/79.5 P

[56] References Cited

U.S. PATENT DOCUMENTS

| | | | |
|---|---|---|---|
| 2,790,749 | 4/1957 | Meine | 260/326 S |
| 3,562,292 | 2/1971 | Grewe et al. | 260/326 S |
| 3,586,696 | 6/1971 | Kerwood et al. | 260/326 S |
| 3,645,987 | 2/1972 | Kerwood | 260/784 |
| 3,687,974 | 8/1972 | Colln | 260/326 S |
| 3,737,438 | 6/1973 | Roos et al. | 260/326 S |
| 3,947,429 | 3/1976 | Sagawa et al. | 260/784 |

*Primary Examiner*—Ronald W. Griffin
*Attorney, Agent, or Firm*—Connolly and Hutz

[57] ABSTRACT

Sulphenamides are obtained by reacting N-chlorothiophthalimide with compounds containing one or two olefinic double bonds. These products retard vulcanization of natural or synthetic rubber.

6 Claims, No Drawings

SULPHENAMIDES, THEIR PRODUCTION AND THEIR USE AS VULCANIZATION RETARDERS

This invention relates to sulphenamides obtained by the addition of N-chlorothiophthalimide to compounds containing one or two olefinic double bonds. In cases where monoolefines are used for the addition reaction, the sulphenamides according to the invention may be represented by the following general formula:

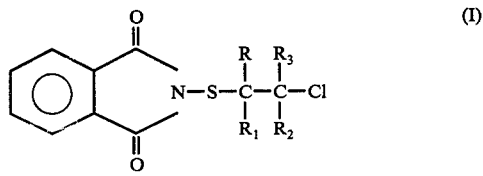

in which:

R, $R_1$, $R_2$, $R_3$ are the same or different and represent H, a straight-chain or branched-chain alkyl radical with 1 to 24 carbon atoms, a cycloalkyl radical which contains from 4 to 10 ring carbon atoms and which may be substituted by straight-chain or branched alkyl radicals with 1 to 12 carbon atoms or by aryl radicals containing 6 to 10 carbon atoms; an aryl radical with 6 or 10 ring carbon atoms which may be substituted by alkyl radicals with 1 to 6 carbon atoms or by chlorine or bromine, cyano or nitro groups or aromatic acyl radicals with 7 or 11 carbon atoms; a nitrile group, chlorine or bromine or aliphatic acyl radicals with 1 to 10 carbon atoms or aromatic acyl radicals with 7 or 11 carbon atoms, a carboxylic acid ester group with 1 to 4 carbon atoms in the alcohol component, an alkoxy radical with 1 to 6 carbon atoms; acyloxy radicals whose aliphatic carboxylic acid component contains 1 to 10 carbon atoms or whose aromatic carboxylic acid component contains 7 or 11 carbon atoms, or a heterocyclic radical with 5 to 10 ring carbon atoms which, in addition to carbon, may also contain 1 or 2 oxygen, nitrogen or sulphur atoms and which may optionally be substituted by alkyl radicals with 1 to 6 carbon atoms or aryl radicals with 6 or 10 carbon atoms.

In addition, $R_1$ together with $R_2$ may form a 4- to 12-membered alicyclic ring system optionally substituted by alkyl radicals containing 1 to 12 carbon atoms or aryl radicals containing 6 or 10 carbon atoms, or a heterocyclic ring system with 5 to 10 ring carbon atoms which, in addition to carbon, may also contain 1 or 2 oxygen, nitrogen or sulphur atoms and which may be substituted by chlorine, bromine or alkyl radicals containing 1 to 12 carbon atoms.

The invention also relates to the production of the above sulphenamides by the addition of N-chlorothiophthalimide with compounds containing 1 or 2 olefinic double bonds, preferably one double bond.

The N-chlorothiophthalimide required as starting material may be obtained by chlorinating N,N'-dithiobisphthalimide at temperatures in the range from 20 to 100° C. N,N'-Dithio-bis-phthalimide is described in Canadian Journal of Chemistry, Vol. 44, page 2172 (1966).

In addition to chlorine, it is also possible to use other chlorinating agents, in particular sulphuryl chloride.

In general, the reaction is carried out with stoichiometric quantities of N,N'-dithio-bis-phthalimide and chlorine or chlorinating agent, although it may also be carried out with a relatively small excess, more especially less than 10 mol or val %, of one or the other starting component.

The reaction may also be carried out in the presence of a solvent which is inert with respect to chlorine under the reaction conditions. Suitable solvents of this kind are, for example, per-halogenated aliphatic hydrocarbons, more especially tetrachloromethane, aromatic hydrocarbons such as benzene, nitrobenzene and, preferably, aromatic chlorinated hydrocarbons, more especially chlorobenzene and dichlorobenzene.

In general, the reaction is carried out by suspending and/or dissolving the N,N'-dithio-bis-phthalimide in the solvent and adding chlorine or the chlorinating agent while stirring. On completion of the addition, the mixture is left to react for a while, after which the solvent is completely or partly distilled off, optionally in vacuo, and the reaction product is isolated. It can be of particular advantage to distil off only part of the solvent and subsequently to use a different solvent which has little or no dissolving effect on the reaction product, chlorothio-N-phthalimide, but is miscible with the solvent used during the reaction.

To this end, it is also possible with advantage to use conventional inert solvents of the type which are not inert with respect to chlorine under the reaction conditions, for example aliphatic hydrocarbons and mixtures such as petroleum ether, light petrol. In this way, it is possible for example to precipitate the reaction product and to isolate it from the reaction mixture of from the solvent in advantageous manner by known methods, for example by filtration, centrifuging, etc..

In general, the reaction is carried out under normal pressure, although it may also be carried out either under reduced or elevated pressure. It may be of particular advantage to carry out the reaction under an elevated pressure of up to about 10 bars and more especially of up to about 2 bars in order to obtain a higher reaction velocity and a shorter reaction time.

The process according to the invention may of course also be carried out continuously, for example in a reaction tube, in a cascade of reaction vessels or in any other apparatus of the type commonly used for continuous processes.

The second starting material required is selected from the following:

1. Acyclic compounds with 1 or 2 olefinic double bonds which contain from 2 to 20 carbon atoms, preferably from 2 to 10 carbon atoms, and which may optionally be substituted by cycloalkyl radicals containing 4 to 10 carbon atoms. The acyclic compounds containing 1 to 2 olefinic double bonds may also be substituted by aryl radicals containing 6 or 10 ring carbon atoms which may be substituted by chlorine or bromine, cyano or nitro groups or by aliphatic acyl radicals containing 1 to 10 carbon atoms or by aromatic acyl radicals containing 7 or 11 carbons atoms. Other substituents are: chlorine, bromine, nitrile groups, aliphatic acyl radicals with 1 to 10 carbon atoms or aromatic acyl radicals with 7 or 11 carbon atoms, a carboxylic acid ester group with 1 to 4 carbon atoms in the alcohol component, an alkoxy radical with 1 to 6 carbon atoms, also acyloxy radicals whose aliphatic carboxylic acid component contains from 1 to 10 carbon atoms or whose aromatic carboxylic acid component contains 7 or 11 carbon atoms.

2. Cyclic olefins with 4 to 10 ring carbon atoms which may optionally be substituted by alkyl radicals containing 1 to 12 carbon atoms or by aryl radicals with 6 or 10 carbon atoms.
3. Heterocyclic olefins with 5 to 10 ring atoms which, in addition to carbon, may also contain 1 or 2 oxygen, nitrogen or sulphur atoms and which may optionally be substituted by alkyl radicals containing 1 to 6 carbon atoms or by aryl radicals containing 6 or 10 carbon atoms.

The following are examples of olefins of this kind: ethylene, propene, n-butylene, i-butylene, n-pentene, 2,3-dimethyl-1-butene, 2,2,4-trimethyl-3-pentene, 2,2,4-trimethyl-4-pentene, 2,4,4-trimethyl-1-pentene, 2,4,4-trimethyl-2-pentene, tripropylene, tetrapropylene, 2,4,4,6,6-pentamethyl-1-heptene, tetraisobutylene, butadiene, isoprene, 2,3-dimethyl butadiene, chloroprene, styrene, α-methyl styrene, divinyl benzene, diisopropenyl benzene, stilbene, vinyl chloride, allyl chloride, allyl bromide, methallyl chloride, methallyl bromide, vinylidene chloride, trichloroethylene, 2,3,4-trichloro-1-butene, 1,3-dichloro-2-butene, 1-bromo-2-butene, acrylonitrile, crotonic acid nitrile, 1,4-dicyano-2-butene, methacrylonitrile, vinyl methyl ketone, mesityl oxide, methyl butenone, methyl acrylate, ethyl acrylate, methyl methacrylate, ethyl methacrylate, crotonic acid methyl ester, crotonic acid ethyl ester, oleic acid ethyl ester, maleic acid methyl ester, fumaric acid ethyl ester, vinyl isopropyl ether, vinyl isobutyl ether, acetic acid vinyl ester, allyl acetate, 1,2-diacetoxy propene, 1,1-diacetoxy-2-propene, cyclobutene, cyclopentene, cyclohexene, methyl cyclohexene, dodecyl cyclohexene, cycloheptene, cyclooctene, pinene, norbornene, camphene, indene, dihydronaphthalene, cyclohexadiene, norbornadiene, vinyl cyclohexene, ethylidene norbornene, dicyclopentadiene, cyclopentadiene, dihydrofuran, dihydropyran, butadiene sulphone, 2-ethoxy-dihydropyran, tetrahydrophthalic acid anhydride, 1,2-diphenyl-Δ³-pyrazoline.

Reaction of the N-chlorothiophthalimide with the olefins in accordance with the invention may be carried out in the presence or in the absence of solvents. Suitable solvents are solvents which do not react with the N-chlorothiophthalimide, such as for example chlorobenzene, dichlorobenzene, toluene, nitrobenzene, chloroform, methylene chloride, tetrachloromethane, trichloroethene, tetrachloroethene, dioxan, tetrahydrofuran, dimethyl formamide and dimethyl sulphoxide. It is preferred to use the solvents in which the N-chlorothiophthalimide is produced, such as for example chlorobenzene, dichlorobenzene, nitrobenzene or halogenated aliphatic hydrocarbons.

The reaction is carried out with 1 to 1.2 mols of monoolefin and preferably with 1 mol of monoolefin or with 0.5 to 1 mol of diolefin and preferably with 0.5 mol of diolefin per mol of N-chlorothiophthalimide. The reaction temperature is in the range from −20° to +60° C and preferably in the range from 0° to 40° C. The reaction pressure is in the range from 1 to 6 bars, although the reaction is preferably carried out under normal pressure.

The components may be added in any order. It is preferred initially to prepare a solution of the N-chlorothiophthalimide and to introduce the olefin into the solution thus prepared without previously isolating the N-chlorothiophthalimide. Liquid olefins are generally added in pure form or in the form of solutions, whilst solid olefins are generally added in the form of solutions, whilst gaseous olefins are introduced into the reaction mixture. The reaction products are isolated by known methods. They are generally colourless and odourless, storable solid compounds.

The following new sulphenamides for example may be produced by this process: 2-chloroethylthiophthalimide, 2-chloro-2-methylethylthiophthalimide, 2-chloro-2-butyl thiophthalimide, 2-chloro-2,2-dimethylethylthiophthalimide, 2-chloro-1,1-dimethylethylthiophthalimide, 2-chloro-2-isopropyl-2-methylethylthiophthalimide, 2-chloro-1,1,2-trimethylethylthiophthalimide, 2-chloro-1,2,2-trimethylethylthiophthalimide, 2-chloro-2-bromomethyl-1-methylethylthiophthalimide, 2-chloro-1-chloromethylethylthiophthalimide, 2-chloro-2-phenylethylthiophthalimide, 2-chloro-2-phenyl-2-methylethylthiophthalimide, 2-chlorocyanoethylthiophthalimide, 2-chloroacetylethylthiophthalimide, 2-chlorocarbethoxyethylthiophthalimide, 2-chloromethoxyethylthiophthalimide, 2-chloroacetoxyethylthiophthalimide, 2-chlorocyclobutylthiophthalimide, 2-chlorocyclopentylthiophthalimide, 2-chlorocyclohexylthiophthalimide, 2-chlorocycloheptylthiophthalimide, 2-chloronorbornylthiophthalimide, 2-chloroindanylthiophthalimide, 2-chloro-Δ³-cyclopentenylthiophthalimide, 2-chlorotetrahydropyranylthiophthalimide; also addition products of N-chlorothiophthalimide with compounds containing 2 olefinic double bonds, for example, butadiene, isoprene, 2,3-dimethyl butadiene, chloroprene, divinyl benzene, diisopropenyl benzene, cyclohexadiene, norbornadiene, vinyl cyclohexene, ethylidene norbornene, dicyclopentadiene or cyclopentadiene.

The addition of N-chlorothiophthalimide with compounds containing two olefinic double bonds generally leads to mixtures of structurally isomeric mono- and bis-sulphenamides. Furthermore, addition of the N-chlorothiophthalimide may be carried out both in accordance with Markownikow's rule and contrary to that rule, just as in the case of compounds containing one olefinic double bond. There is no need for mixtures of this kind to be separated for commercial application, for example as vulcanization retarders.

The present invention also relates to the use of the new sulphenamides as vulcanization retarders in the production and processing of mixtures based on natural or synthetic rubber.

It has surprisingly been found that the sulphenamides according to the invention are particularly suitable for use as vulcanization retarders in the production and processing of mixtures containing natural or synthetic rubber by known methods.

Rubbers suitable for the production and processing of mixtures based on natural or synthetic rubber are, for example, natural rubber or synthetic rubber-like polymers obtained, for example, from conjugated diolefins, such as butadiene, dimethyl butadiene, chloroprene, isoprene and homologues thereof, or copolymers of these conjugated diolefins with polymerisable vinyl compounds, such as styrene, α-methyl styrene, acrylonitrile, methacrylonitrile, acrylates, methacrylates, also terpolymers of ethylene, propylene and at least one non-conjugated diene, for example dicyclopentadiene, 5-ethylidene-2-norbornene or 1,4-hexadiene.

The retarders used in accordance with the invention may be worked into the rubber in the usual way, for example on mixing rolls or in an internal mixer, and are preferably added before or at the same time as the other constituents. However, they may also be added as the final constituent of the mixture.

The retarders according to the invention are used preferably in quantities of from 0.05 to 5.0 % by weight and more preferably in quantities of from 0.1 to 1.5 % by weight, based on the rubber. The actual dosage used may be well determined by a person skilled in the art and depends on what he has in mind.

The rubber mixtures to be treated contain the usual vulcanization additives, such as vulcanization agents and accelerators. The vulcanization agent, for example sulphur, may be used in the usual quantity for vulcanization, generally in a quantity of from 0.2 to 5.0 % by weight, based on the rubber. Examples of accelerators are thiazoles, such as 2-mercaptobenzthiazole or dibenzothiazyl disulphide, sulphenamides such as benzothiazyl-2-cyclohexyl sulphenamide, benzthiazyl-2-tert.-butyl sulphenamide or benzthiazyl sulphene morpholide, guanidines such as diphenyl guanidine or di-o-tolyl guanidine, dithiocarbamates such as zinc diethyl dithiocarbamate, and thiurams such as tetramethyl thiuram disulphide or tetramethyl thiuram monosulphide.

It is also possible to use mixtures of accelerators. The accelerators are generally used in quantities of from 0.05 to 5% by weight, based on the rubber.

The rubber mixture may also contain other known additives, for example active or inactive fillers such as chalk or carbon black, antioxidants, anti-ozonants, waxes, pigments, zinc oxide, fatty acids such as stearic acid, or processing oils.

The rubber may be vulcanized by heating to the usual temperatures, preferably to a temperature of from 120° C to 170° C, although vulcanization may even be carried out at higher or lower temperatures.

The invention is illustrated by but no means limited to the following Examples. Unless otherwise stated, the values quoted in the Tables of the Practical Examples are parts by weight, based on 100.0 parts by weight of rubber.

The following mixtures were prepared on mixing rolls:

| Application Mixture No. | 1 | 2 | 3 | 4 | 5 | 6 |
|---|---|---|---|---|---|---|
| Natural rubber, smoked sheets | 100.0 | 100.0 | 100.0 | 100.0 | 10.0 | 100.0 |
| Zinc oxide | 5.0 | 5.0 | 5.0 | 5.0 | 5.0 | 5.0 |
| Stearic acid | 3.0 | 3.0 | 3.0 | 3.0 | 3.0 | 3.0 |
| Aromatic mineral oil plasticiser | 2.5 | 2.5 | 2.5 | 2.5 | 2.5 | 2.5 |
| Highly abrasion-resistant furnace black | 45.0 | 45.0 | 45.0 | 45.0 | 45.0 | 45.0 |
| Naphthenic mineral oil plasticiser | 2.5 | 2.5 | 2.5 | 2.5 | 2.5 | 2.5 |
| N-isopropyl-N'-phenyl-p-ohenylene diamine | 1.5 | 1.5 | 1.5 | 1.5 | 1.5 | 1.5 |
| Sulphur | 2.3 | 2.3 | 2.3 | 2.3 | 2.3 | 2.3 |
| N-cyclohexyl-2-benzthiazyl sulphenamide | 0.5 | 0.5 | 0.5 | 0.5 | 0.5 | 0.5 |
| 2-chlorocyclohexylthiophthalimide | — | 0.5 | — | — | — | — |
| 2-chlorocyclopentyl thiophthalimide | — | — | 0.5 | — | — | — |
| 2-chloroethyl-thiophthalimide | — | — | — | 0.5 | — | — |
| 2-chloro-2,2-dimethylethylthiophthalimide | — | — | — | — | 0.5 | — |
| 2-chloro-1,2,2-trimethylethylthiophthalimide | — | — | — | — | — | 0.5 |

In order to determine the retarding effect of the sulphenamides according to the invention, the mixtures obtained were tested by means of a vulcameter, System BAYER (cf. H. Kramer, Gummi-Asbest-Kunststoffe 23, No. 1/1970, pages 22 et seq.). The following test methods were used:

Precure time $t_s$:
Determined on the same lines as the Mooney Scorch Time (DIN 53 524): Time taken by the vulcameter curve to rise 20 mm above the minimum.

Cure time $t_{90}$:
Time taken by the vulcameter curve to reach 90 % of the maximum value. : Maximum vulcameter reading, starting from the minimum level (Fa) of the vulcameter curve (cf. DIN 53 529).

Table

| Mixture No. | Vulcanization retarder | Precure time (mins) at 120° C | Precure time (mins) at 140° C | Full-cure time $t_{90}$ (mins) | Full-cure time Fa/Fe (mm) |
|---|---|---|---|---|---|
| 1 | none | 38.6 | 9.9 | 29.0 | 127 |
| 2 | 2-chlorocyclohexyl-thiophthalimide | 69.3 | 16.4 | 35.3 | 124 |
| 3 | 2-chlorocyclopentyl-thiophthalimide | 67.4 | 16.4 | 34.3 | 123 |
| 4 | 2-chloroethylthio-phthalimide | 48.6 | 12.1 | 32.0 | 133 |
| 5 | 2-chloro-2,2-dimethyl-ethylthiophthalimide | 55.9 | 13.9 | 33.1 | 131 |
| 6 | 2-chloro-1,2,2-tri-methylethylthio-phthalimide | 68.2 | 16.2 | 35.1 | 126 |

The test results, especially the precure times, clearly show that the sulphenamides according to the invention are vulcanization retarders with a relatively strong effect.

EXAMPLE 1

Addition to cyclohexene 35.6 g (0.1 mol) of N,N'-dithio-bis-phthalimide were introduced into 200 ml of chlorobenzene, followed by the introduction at 35° C of 7.1 g (0.1 mol) of chlorine. After stirring for 1 hour at 35° C, 17.2 g (0.21 mol) of cyclohexene were added dropwise to the clear solution, the temperature being kept below 40° C optionally be gentle cooling. The decoloured solution was stirred for 1 hour at room temperature and subsequently concentrated in vacuo. The concentrate was shaken with 300 ml of light petrol and subsequently filtered off under suction. 56 g of the compound, which melted at 127° C to 130° C, were obtained after drying. Melting point after recrystallization from acetonitrile: 135° C.

$C_{14}H_{14}ClNO_2S$ (295.8) calculated: C 56.9 H 4.8 Cl 12.0 N 4.7 S 10.8; found: C 57.2 H 4.7 Cl 11.9 N 4.9 S 11.2

The addition products (B) summarised in Table I were similarly obtained from the olefins (A).

TABLE 1

| Example No. | A | B | Yield | m.p. | Elemental analysis |
|---|---|---|---|---|---|
| 2 |  | 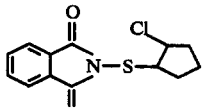 | 90 % | 96° | Calculated: C 55.4 H 4.3 Cl 12.6<br>Found: 55.4 4.3 12.3<br>Calculated: N 5.0 S 11.4<br>Found: 5.4 11.7 |
| 3 |  | 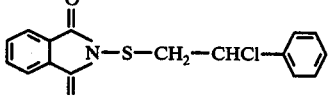 | 90 % | 93° | Calculated: C 60.5 H 3.8 Cl 11.2<br>Found: 60.6 3.9 11.2<br>Calculated: N 4.4 S 10.1<br>Found: 4.7 10.3 |
| 4 |  | 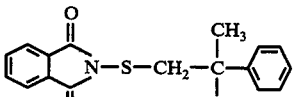 | 90 % | 93° | Calculated: C 61.5 H 4.3 N 4.2<br>Found: 61.4 4.4 4.4<br>Calculated: Cl 10.7 S 9.7<br>Found: 10.5 9.6 |
| 5 | $CH_2=CH_2$ | 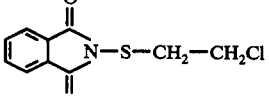 | 95 % | 119–120° | Calculated: C 49.7 H 3.3 Cl 14.7<br>Found: 49.6 3.6 14.2<br>Calculated: N 5.8 S 13.2<br>Found: 6.0 13.2 |
| 6 | 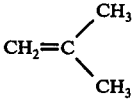 | 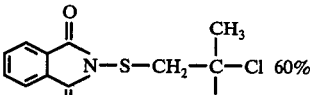 | 73 % | 100–113° | Calculated: C 53.5 H 4.5 Cl 13.1<br>Found: 53.6 4.5 13.0<br>Calculated: N 5.2 S 11.9<br>Found: 5.3 11.7 |
| 7 | $CH_3-CH=CH_2$ | 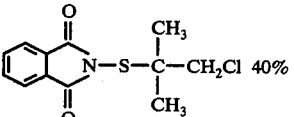 | 60 % | 103° | Calculated: C 51.6 H 3.9 Cl 13.9<br>Found: 51.4 4.0 13.6<br>Calculated: N 5.5 S 12.5<br>Found: 5.6 12.3 |
| 8 | 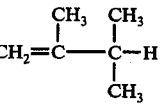 | 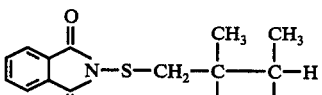 | 75 % | 114–117° | Calculated: C 56.5 H 5.4 C 11.9<br>Found: 56.4 5.2 11.9<br>Calculated: N 4.7 S 10.7<br>Found: 5.0 10.7 |
| 9 | 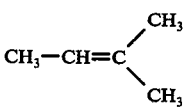 | 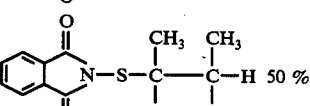 | 78 % | 109–112° | Calculated: C 55.0 H 5.0 Cl 12.5<br>Found: 55.1 4.9 11.9<br>Calculated: N 5.0 S 11.3<br>Found: 4.9 11.7 |
| 10 | $CH_3-CH=CH-CH_2Br$ | 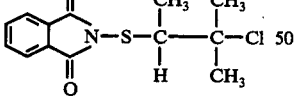 | 60 % | 107° | Calculated: C 41.3 H 3.2 Cl 10.2<br>Found: 41.6 3.3 10.2<br>Calculated: N 4.0 S 9.2 Br 22.9<br>Found: 4.1 9.5 22.5 |
| 11 | $CH_3-CH=CH-CH_2Br$ | 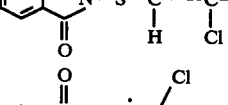 | 79 % | 123–126° | Calculated: C 62.0 H 3.0 Cl 10.8<br>Found: 62.0 3.6 10.4<br>Calculated: N 4.2 S 9.7<br>Found: 4.2 9.7 |
| 12 | $CH_2-CH-O-\overset{O}{\overset{\|}{C}}-CH_3$ | 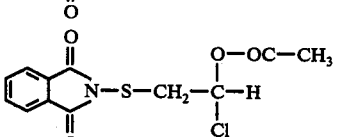 | 91 % | 142–145° | Calculated: C 49.3 H 3.4 Cl 12.1<br>Found: 49.3 3.9 11.8<br>Calculated: N 4.8 S 10.4<br>Found: 4.9 10.8 |

TABLE 1-continued

| Example No. | A | B | Yield | m.p. | Elemental analysis |
|---|---|---|---|---|---|
| 13 |  | 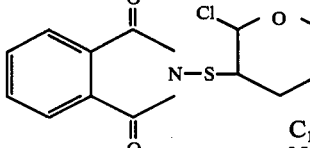 | 45 % | 120–145° | Calculated: C 52.5 H 4.1 Cl 11.9<br>Found: 52.5 3.9 11.7<br>Calculated: N 4.7 S 10.8<br>Found: 4.1 10.6 |

$C_{13}H_{10}ClNO_2S$ (279.8) calculated: C 55.8 H 3.6 Cl 12.7 N 5.0 S 11.4; found: 55.5 3.1 13.1 5.0 11.5.

EXAMPLE 14

Addition to allyl chloride 35.6 g (0.1 mol) of N,N'-dithio-bis-phthalimide were initially introduced into 200 ml of chlorobenzene, followed by the introduction at 35° C of 7.1 g (0.1 mol) of chlorine. After stirring for another hour at 35° C, 16.8 g (0.22 mol) of allyl chloride were added to the clear solution. The mixture was stirred for another 24 hours at room temperature and the crystals formed subsequently filtered off under suction. Yield 36 g, corresponding to 62% of the theoretical yield. m.p.: 129°–131° C (from toluene)

$C_{11}H_9Cl_2NO_2S$ (290.2) calculated: C 45.6 H 3.1 Cl 24.4 N 4.8 S 11.0 found: 45.3 3.1 23.6 4.8 11.0

EXAMPLE 15

Addition with both double bonds of norbornadiene 35.6 g (0.1 mol) of N,N'-dithio-bis-phthalimide were initially introduced into 200 ml of chlorobenzene, followed by the introduction at 35° C of 7.1 g (0.1 mol) of chlorine. After stirring for another hour at 35° C, 9.2 g of norbornadiene were added dropwise to the solution. The mixture was stirred for 24 hours at room temperature, followed by the addition of 200 ml of petroleum ether. After filtration under suction, the product was washed once with 50 ml of petroleum ether. After drying, the substance had a melting point of 185° C. Yield: 32 g, corresponding to 61.5 % of the theoretical yield.

$C_{23}H_{16}Cl_2N_2O_4S_2$ (519.4) calculated: C 53.2 H 3.1 Cl 13.7 N 5.4 S 12.3; found: 53.6 3.1 13.1 5.4 12.4.

EXAMPLE 16

Addition with both double bonds of isoprene

The procedure of Example 15 using 6.8 g (0.1 mol) of isoprene instead of norbornadiene gave the addition product with isoprene with a melting point of 190° C (from glycol monomethyl ether). Yield 17 g, corresponding to 34.5 % of the theoretical yield.

$C_{21}H_{16}Cl_2N_2O_4S_2$ (495.4) calculated: C 50.9 H 3.3 Cl 14.3 N 5.7 S 12.9; found: 51.3 3.3 14.2 5.8 12.8

EXAMPLE 17

Addition with one double bond of cyclopentadiene 35.6 g (0.1 mol) of N,N'-dithio-bis-phthalimide were initially introduced into 200 ml of chlorobenzene, followed by the introduction of 7.1 g of chlorine at 35° C. After stirring for another hour at 35° C, the clear solution formed was added dropwise at 0° C to a solution of 14.5 g of cyclopentadiene in 50 ml of chlorobenzene. After stirring for another 5 hours at room temperature, half of the chlorobenzene was evaporated off in vacuo and 100 ml of light petrol added to the residue. After filtration under suction and recrystallization from cyclohexane, the product melted at 72 to 76° C. Yield 12 g, corresponding to 21.5 % of the theoretical yield.

EXAMPLE 18

Example 18 demonstrates the preparation of the compound of Example 1 by the successive reaction of phthalimide with $S_2Cl_2$, chlorolysis of the N,N'-dithiophthalimide formed as intermediate and subsequent addition of the N-chlorothiophthalimide with cyclohexene in a so-called "one-pot process":

147 g (1 mol) of phthalimide were initially introduced into 1 liter of chlorobenzene, followed by the addition of 150 g of dimethyl benzyl amine. The mixture was heated to 45° C, followed by the dropwise addition over a period of 3 hours with thorough stirring of a solution of 67.5 g (0.5 mol) of disulphur dichloride in 70 ml of chlorobenzene. After stirring for another 2 hours at 45° C, the mixture was cooled to 35° C and 35.5 g (0.5 mol) of chlorine were introduced into it at that temperature. After the chlorine had been introduced, the mixture was stirred for 1 hour at 35° C, followed by the dropwise addition of 90 g of cyclohexene. After stirring for another 2 hours, 1 litre of water was added, a small quantity of unreacted phthalimide was filtered off under suction and the organic phase separated off in a separation funnel. It was dried over $Na_2SO_4$ and the chlorobenzene concentrated by evaporation in vacuo. The residue was stirred with 200 ml of light petrol and filtered off under suction. 250 g (85 % of the theoretical yield) of α-chlorocyclohexyl thiophthalimide, in the form of a colourless powder melting at 125° to 131° C, were obtained in this way.

We claim:

1. A sulphenamide produced by the addition reaction of N-chlorothiophthalimide and a compound selected from the group consisting of acyclic compounds having 1 to 2 olefinic double bonds and containing from 2 to 20 carbon atoms; cyclic olefins having 1 to 2 olefinic double bonds and having 4 to 10 ring carbon atoms and heterocyclic olefins having 1 to 2 olefinic double bonds and from 5 to 10 ring carbon atoms of which from 1 to 2 are oxygen, nitrogen, or sulphur and the balance are carbon.

2. The sulphenamide of claim 1 wherein said selected member of said group has one olefinic double bond.

3. A process for producing a sulphenamide of claim 2 which comprises contacting 1 mol of N-chlorothiophthalimide with from 1.2 to 1 mol of said compound selected from said group at a temperature of from −20° to 60° C.

4. The sulphenamide of claim 1 wherein said selected member of said group has two olefinic double bonds.

5. A process for producing a sulphenamide of claim 4 which comprises contacting 1 mol of N-chlorothiophthalimide with 0.5 to 1 mol of said compound selected from said group at a temperature of from −20° to 60° C.

6. A process for retarding vulcanization of a natural or synthetic rubber which comprises adding to said rubber a vulcanization retarding amount of a sulphenamide of claim 1.

* * * * *